United States Patent
Yeh (10) Patent No.: US 9,283,349 B2
(45) Date of Patent: Mar. 15, 2016

(54) METHODS AND APPARATUS FOR DEVICE BASED PREVENTION OF KINETOSIS

(75) Inventor: James Yeh, Berkeley, CA (US)

(73) Assignee: MobiTV, Inc., Emeryville, CA (US)

( * ) Notice: Subject to any disclaimer, the term of this patent is extended or adjusted under 35 U.S.C. 154(b) by 143 days.

(21) Appl. No.: 13/107,619

(22) Filed: May 13, 2011

(65) Prior Publication Data

US 2012/0289767 A1    Nov. 15, 2012

(51) Int. Cl.
*A61M 21/00* (2006.01)

(52) U.S. Cl.
CPC .......... *A61M 21/00* (2013.01); *A61M 2021/005* (2013.01); *A61M 2021/0044* (2013.01); *A61M 2205/3553* (2013.01); *A61M 2205/3584* (2013.01); *A61M 2205/502* (2013.01); *A61M 2230/63* (2013.01)

(58) Field of Classification Search
CPC ...................... A61M 21/00; A61M 2021/0044
USPC .......................................................... 600/27
See application file for complete search history.

(56) References Cited

U.S. PATENT DOCUMENTS

| 5,805,212 A * | 9/1998 | Fujiwara .................... 348/208.8 |
| 5,966,680 A * | 10/1999 | Butnaru ........................ 702/150 |
| 6,497,649 B2 * | 12/2002 | Parker et al. ..................... 600/27 |
| 2006/0015000 A1 * | 1/2006 | Kim .............................. 600/27 |
| 2007/0034212 A1 * | 2/2007 | Brendley et al. .............. 128/897 |

OTHER PUBLICATIONS

Reschke, et al., "Stroboscopic Vision as a Treatment for Space Motion Sickness," NASA Human Research Program Investigators' Workshop, Feb. 12-14, 2007, 1 page.

* cited by examiner

*Primary Examiner* — John Lacyk
*Assistant Examiner* — Eileen Hyde
(74) *Attorney, Agent, or Firm* — Kwan & Olynick LLP (57) ABSTRACT

Mechanisms are provided for alleviating kinetosis using a mobile device. Motion sensors, gyroscopes, cameras, inertial modules, proximity detectors, global position system (GPS) receivers, orientation sensors, etc., are used to monitor motion that a mobile device user feels through the vestibular system but may not observe. A kinetosis alleviation system generates activity on a mobile device display that simulates the detected motion. In some examples, the activity may be a frame around video or text that shows movement congruent or more congruent with detected motion. In other examples, the activity may be a video or text window itself that moves in a manner congruent with detected motion.

22 Claims, 6 Drawing Sheets

METHODS AND APPARATUS FOR DEVICE BASED PREVENTION OF KINETOSIS

DESCRIPTION OF RELATED ART

The present disclosure relates to techniques and mechanisms for mobile media based prevention of kinetosis.

DESCRIPTION OF RELATED ART

Kinetosis arises when there is incongruity between visually perceived motion and motion sensed through the vestibular system. Kinetosis frequently occurs in relatively enclosed vehicles when occupants are moving but are not observing or can not be observing the actual motion. Kinetosis can also occur when viewers observe motion but do not feel any movement. Kinetosis is often referred to as motion sickness, car sickness, seasickness, simulation sickness, airsickness, etc.

In many instances, kinetosis may prevent individuals from consuming media including text and video in moving environments such as cars, trains, ships, aircraft, etc. Kinetosis may also prevent individuals from enjoying other environments even when not consuming media. Existing mechanisms for alleviating kinetosis are limited. Consequently, techniques and mechanisms are provided for alleviating kinetosis in a variety of environments.

BRIEF DESCRIPTION OF THE DRAWINGS

The disclosure may best be understood by reference to the following description taken in conjunction with the accompanying drawings, which illustrate particular embodiments of the present invention.

DESCRIPTION OF PARTICULAR EMBODIMENTS

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques of the present invention will be described in the context of particular types of motion and devices. However, it should be noted that the techniques and mechanisms of the present invention can be used with a variety of types of motion and devices. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a processor is used in a variety of contexts. However, it will be appreciated that multiple processors can also be used while remaining within the scope of the present invention unless otherwise noted. Furthermore, the techniques and mechanisms of the present invention will sometimes describe two entities as being connected. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

Mechanisms are provided for alleviating kinetosis using a mobile device. Motion sensors, gyroscopes, accelerometers, cameras, inertial modules, proximity detectors, global position system (GPS) receivers, orientation sensors, etc., are used to monitor motion that a mobile device user feels through the vestibular system but may not observe. A kinetosis alleviation system generates activity on a mobile device display that simulates the detected motion. In some examples, the activity may be a frame around video or text that shows movement congruent or more congruent with detected motion. In other examples, the activity may be a video or text window itself that moves in a manner congruent with detected motion.

Particular Embodiments

Kinetosis occurs when a vestibular system including the inner ear senses motion incongruent with motion viewed by an ocular system. Kinetosis may occur when an individual is traveling in a vehicle and does not have a stationary visual point of reference to detect the motion. The visual point of reference may be the horizon, a landmark, a street sign, a building, etc. In many instances, these stationary visual points of reference may not be visible or available. A passenger may be reading on a train, watching a video on an aircraft, or below deck on a ship. Kinetosis is more pronounced when the disparity between motion felt and motion viewed is more significant. If kinetosis becomes severe, nausea and vomiting can result. However, unlike vomiting resulting from toxins or contaminated food, vomiting does not relieve any symptoms of kinetosis.

A variety of remedies are available including natural and chemical based remedies. However, existing remedies have significant limitations. Existing remedies may restrain an individual to acting in a particular way and prevent consumption of media or may involve chemical substances with varying degrees of efficacy. Consequently, mechanisms are provided for alleviating kinetosis through the use of a device.

Motion detectors including gyroscopes, proximity sensors, orientation detectors, global positioning system (GPS) receivers, cameras, and/or a vehicle's own velocity, pitch, altitude, and direction readings are accessed by a mobile device associated with a user. Display activity such as video is generated to simulate the motion that is occurring around the user. According to various embodiments, a user can watch video or read text while the video or text is surrounded with a frame displaying simulated motion that is occurring around the user. The frame may display video that simulates detected motion. In other examples, the window displaying the video itself undergoes simulated motion. Although mechanisms are effective on mobile devices, fixed devices such as displays in cars or airplanes can also benefit from techniques and mechanism for kinetosis alleviation. Fixed devices such as displays in vehicles and aircraft could potentially more easily benefit from velocity, pitch, altitude, and direction readings from the vehicles and aircraft themselves. Mobile devices such as smartphones, tablets, and portable computer systems can more easily benefit from motion detectors, GPS receivers, wireless fidelity (WiFi) receivers, gyroscopes, orientation sensors, included on mobile devices and would use external interfaces to access motion and location information from vehicle systems.

According to various embodiments, a kinetosis alleviation system provides a fixed point of reference such as a video, text, point, line, or an object surrounded by a field that simulates detected motion relative to the fixed point of reference. The simulated detected motion may be depicted using a star field, scenery, clouds, points, lines, textured backgrounds, rolling hills, etc. In particular embodiments, the user can control the saliency, prominence, and significance of the detected motion through customization. In many cases, detected motion need not be simulated perfectly in order to alleviate kinetosis symptoms. It is recognized that passengers in a car on a slightly windy road are less likely to experience kinetosis that passengers in a car jerking back and forth on a one lane, unpaved, mountain pass. Consequently, even simulated motion that incompletely compensates for detected motion can be beneficial. The techniques of the present invention reduce or eliminate the incongruity between detected motion and observed motion.

Figure 1:
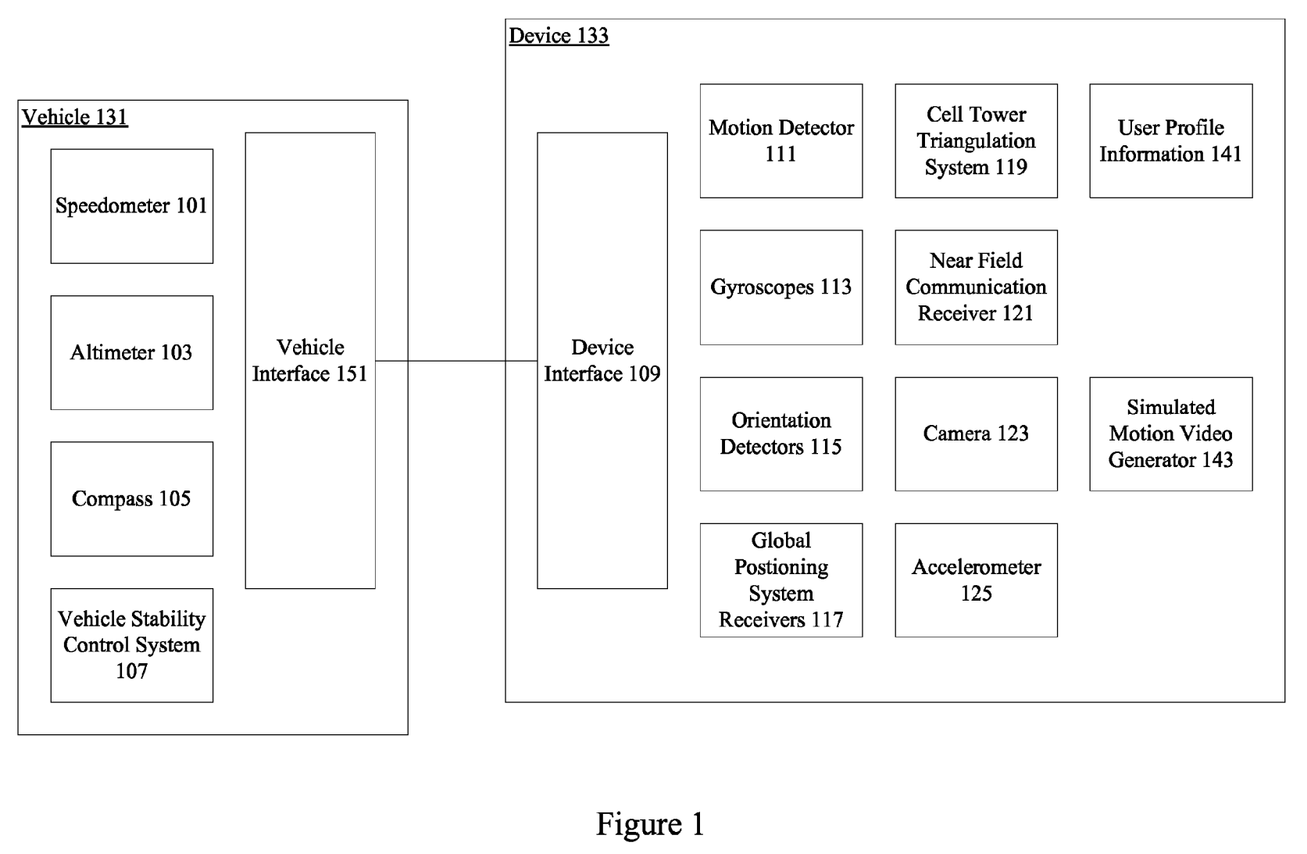
FIG. 1 illustrates a particular example of a system for detecting motion.

FIG. 1 illustrates one example of a kinetosis alleviation system. According to various embodiments, a device 133 such as a mobile device or a fixed device on a vehicle may include a variety of motion detection mechanisms such as motion detector 111, gyroscopes 113, orientation detectors 115, global positioning system receivers 117, cell tower triangulation mechanisms 119, a near field communication receiver 121, a camera 123, and an accelerometer 125. The device may also have a device interface 109 with a vehicle 131 through vehicle interface 151. The vehicle itself may have some of the same motion detection mechanisms as well as some additional motion detection mechanisms. In some examples, the vehicle itself may have a speedometer 101, an altimeter 103, and a compass 105. The vehicle 131 may also have a vehicle stability control system 107 that attempts to maintain a smooth ride in view of rough conditions. The vehicle stability control system 107 may balance cruise liner movements and improve vehicle shock absorption. The vehicle stability control system 107 may also provide data about movement and conditions that a device 133 can use to alleviate kinetosis.

According to various embodiments, a simulated motion video generator 143 continuously receives data from motion detection mechanisms and generates video simulating the detected motion. In one example, detected motion indicates that a viewer is moving at approximately 65 miles per hour eastward along a bumpy road. The motion video generator 143 generates video to simulate 65 mph in the eastward direction with the bumps corresponding to actual detected bumps. In some examples, the magnitude of the simulated bumps or changes in motion is less than that of the detected bumps to compensate for any slight time delay that may result. It should be noted that video may include actual video or any display activity such as a window of text moving in a background or multiple points moving relative to a fixed point. According to various embodiments, the simulated motion may be provided as a service to airlines, cruise lines, or car companies for use in their in seat entertainment units. The simulated motion may also be provided in smartphone, tablet, and mobile computing device applications.

Figure 2:
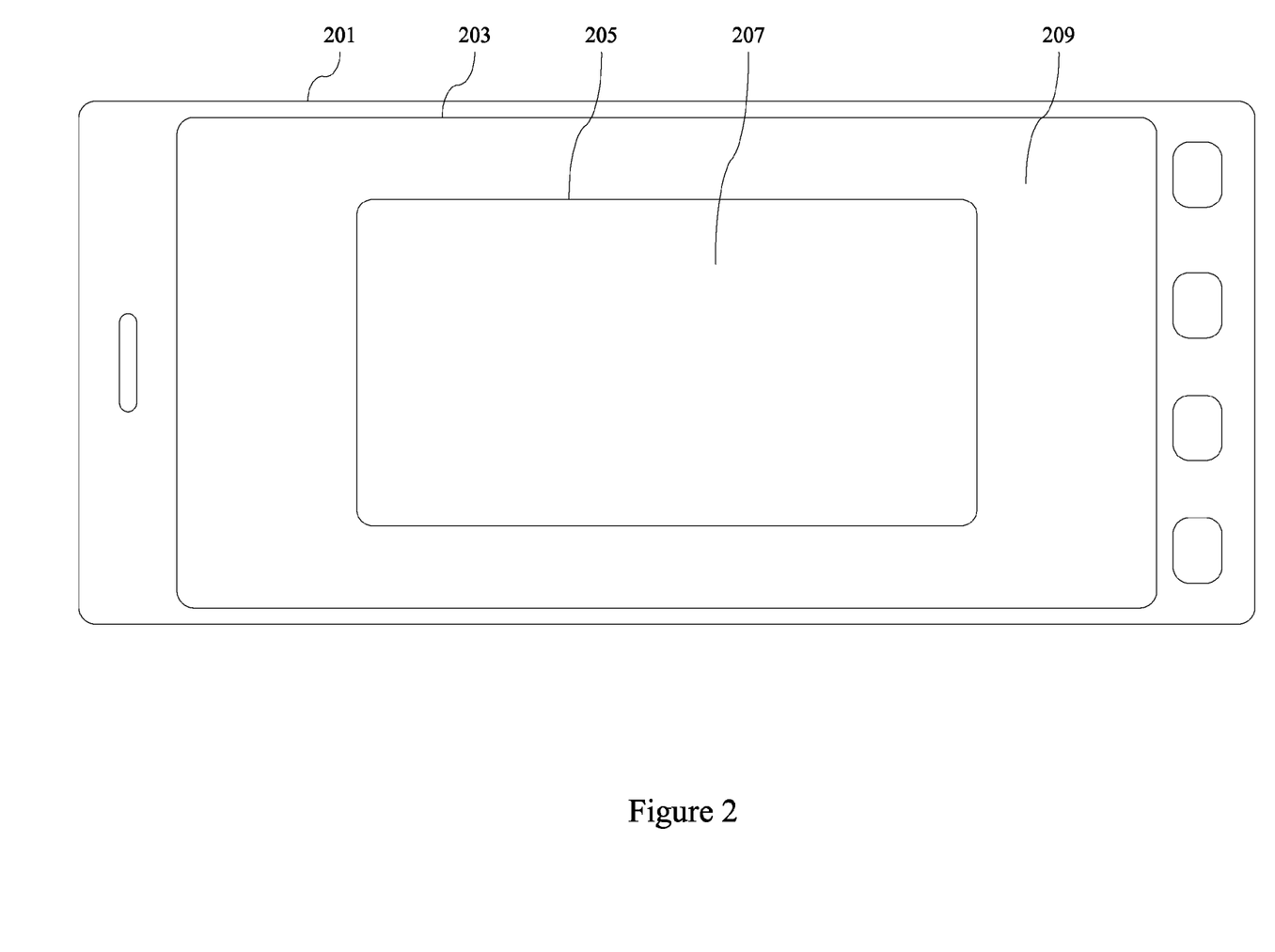
FIG. 2 illustrates a particular example of a system for motion compensation.

FIG. 2 illustrates one example of a display having simulated motion. According to various embodiments, a device 201 may be a smartphone, tablet, mobile computing system, fixed display, terminal, goggles, glasses, helmet, or integrated system. The device 201 includes a display 203. In particular embodiments, the display 203 can be used to display data, tiles, icons, video, text, etc. According to various embodiments, display area 209 is used to show motion simulation activity or video while a window 205 displays content such as text, images, or video in area 207. According to various embodiments, the window 205 may itself also move to simulate motion. The display area 209 may depict actual video, moving points, flowing water, or other images to simulate motion that the viewer may be experiencing.

In some examples, instead of using a frame with area 209 to display simulated motion video, a transparent or semitransparent overlay is generated on top of display 203 to simulate motion. The overlay may depict water droplets that may simulate motion a viewer may be experiencing. According to various embodiments, the device 201 filters common hand movements and attempts to simulate only motion that a viewer is experiencing, not movements resulting from hand jitters. According to various embodiments, hand movements are filtered by calibrating the device to detect hand movements when the viewer is stationary. Common hand movement patterns and sequences can be filtered when a viewer is no longer stationary when viewing text or media materials.

Figure 3:
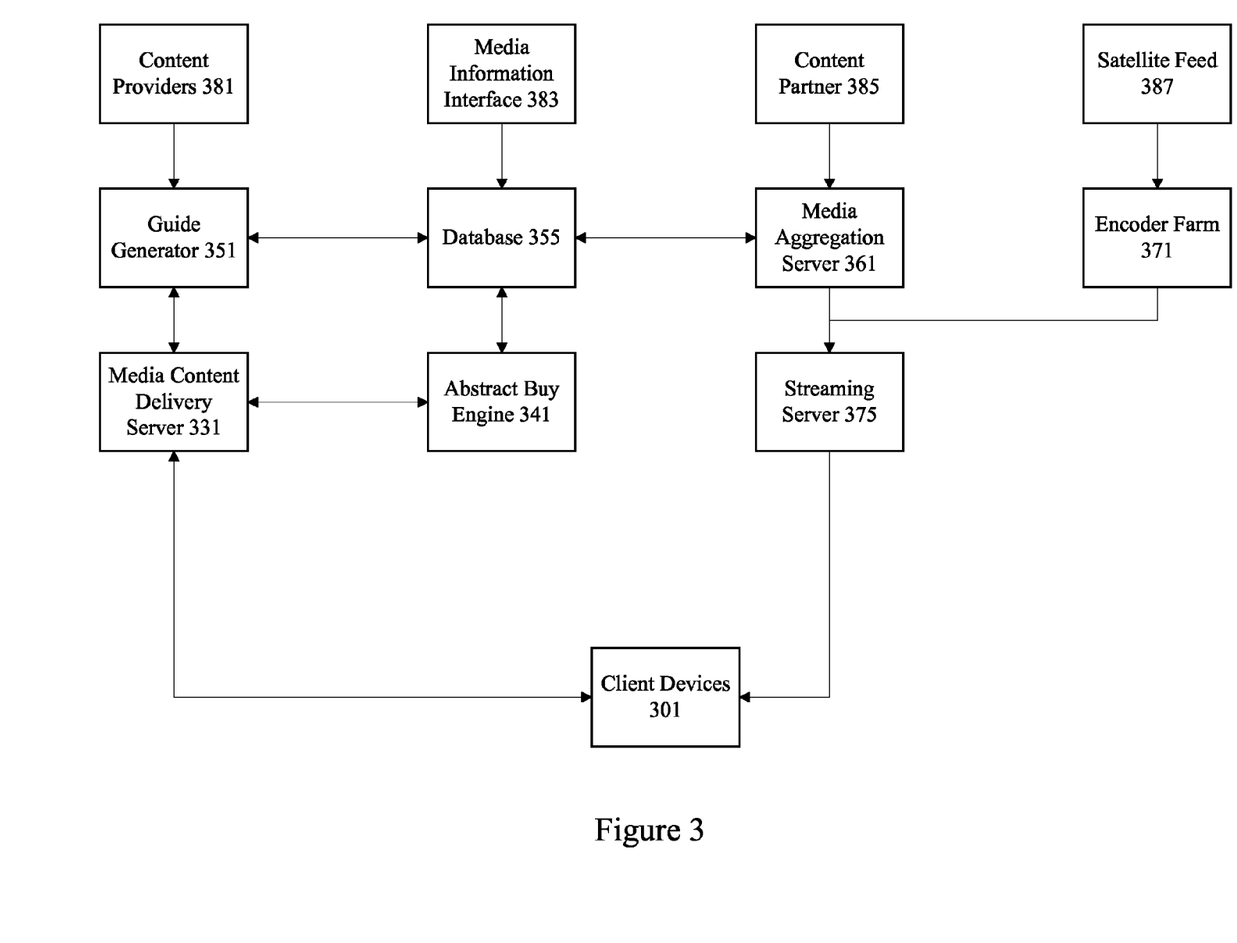
FIG. 3 illustrates a particular example of a media delivery system.

FIG. 3 is a diagrammatic representation showing one example of a network that can use the techniques of the present invention. According to various embodiments, text or media content is provided from a number of different sources 385. Media content may be provided from film libraries, cable companies, movie and television studios, commercial and business users, etc. and maintained at a media aggregation server 361. Any mechanism for obtaining media content from a large number of sources in order to provide the media content to mobile devices in live broadcast streams is referred to herein as a media content aggregation server. The media content aggregation server 361 may be clusters of servers located in different data centers. According to various embodiments, content provided to a media aggregation server 361 is provided in a variety of different encoding formats with numerous video and audio codecs. Media content may also be provided via satellite feed 357. According to various embodiments, media content is categorized by using an IVSSE.

An encoder farm 371 is associated with the satellite feed 387 and can also be associated with media aggregation server 361. The encoder farm 371 can be used to process media content from satellite feed 387 as well as from media aggregation server 361 into potentially numerous encoding formats. According to various embodiments, file formats include open standards MPEG-1 (ISO/IEC 11172), MPEG-2 (ISO/IEC 13818-2), MPEG-4 (ISO/IEC 14496), as well as proprietary formats QuickTime™, ActiveMovie™, and RealVideo™. Some example video codecs used to encode the files include MPEG-4, H.263, and H.264. Some example audio codecs include Qualcomm Purevoice™ (QCELP), The Adaptive Multi—Narrow Band (AMR-NB), Advanced Audio coding (AAC), and AACPlus. The media content may also be encoded to support a variety of data rates. The media content from media aggregation server 361 and encoder farm 371 is provided as live media to a streaming server 375. In one example, the streaming server is a Real Time Streaming Protocol (RTSP) server 375. Media streams are broadcast live from an RTSP server 375 to individual client devices 301. A variety of protocols can be used to send data to client devices.

Possible client devices 301 include personal digital assistants (PDAs), cellular phones, smartphones, personal computing devices, personal computers etc. According to various embodiments, the client devices are connected to a cellular network run by a cellular service provider. In other examples, the client devices are connected to an Internet Protocol (IP) network. Alternatively, the client device can be connected to a wireless local area network (WLAN) or some other wireless network. Live media streams provided over RTSP are carried and/or encapsulated on one of a variety of wireless networks.

The client devices are also connected over a wireless network to a media content delivery server 331. The media content delivery server 331 is configured to allow a client device 301 to perform functions associated with accessing live media streams. For example, the media content delivery server allows a user to create an account, perform session identifier assignment, subscribe to various channels, log on, access program guide 3, obtain information about media content, etc. According to various embodiments, the media content delivery server does not deliver the actual media stream, but merely provides mechanisms for performing operations associated with accessing media. In other implementations, it is possible that the media content delivery server also provides media clips, files, and streams. The media content delivery server is associated with a guide generator 351. The guide generator 351 obtains information from disparate sources including content providers 381 and media information sources 383. The guide generator 351 provides program guides to database 355 as well as to media content delivery server 331 to provide to client devices 301.

According to various embodiments, guide generator 351 is connected to a media content delivery server 331 that is also associated with an abstract buy engine 341. The abstract buy engine 341 maintains subscription information associated with various client devices 301. For example, the abstract buy engine 341 tracks purchases of premium packages.

The media content delivery server 331 and the client devices 301 communicate using requests and responses. For example, the client device 301 can send a request to media content delivery server 331 for a subscription to premium content. According to various embodiments, the abstract buy engine 341 tracks the subscription request and the media content delivery server 331 provides a key to the client device 301 to allow it to decode live streamed media content. Similarly, the client device 301 can send a request to a media content delivery server 331 for a most-watched program guide for its particular program package. The media content delivery server 331 obtains the guide data from the guide generator 351 and associated database 355 and provides appropriate guide information to the client device 301.

Although the various devices such as the guide generator 351, database 355, media aggregation server 361, etc. are shown as separate entities, it should be appreciated that various devices may be incorporated onto a single server. Alternatively, each device may be embodied in multiple servers or clusters of servers. According to various embodiments, the guide generator 351, database 355, media aggregation server 361, encoder farm 371, media content delivery server 331, abstract buy engine 341, and streaming server 375 are included in an entity referred to herein as a media content delivery system.

Figure 4:
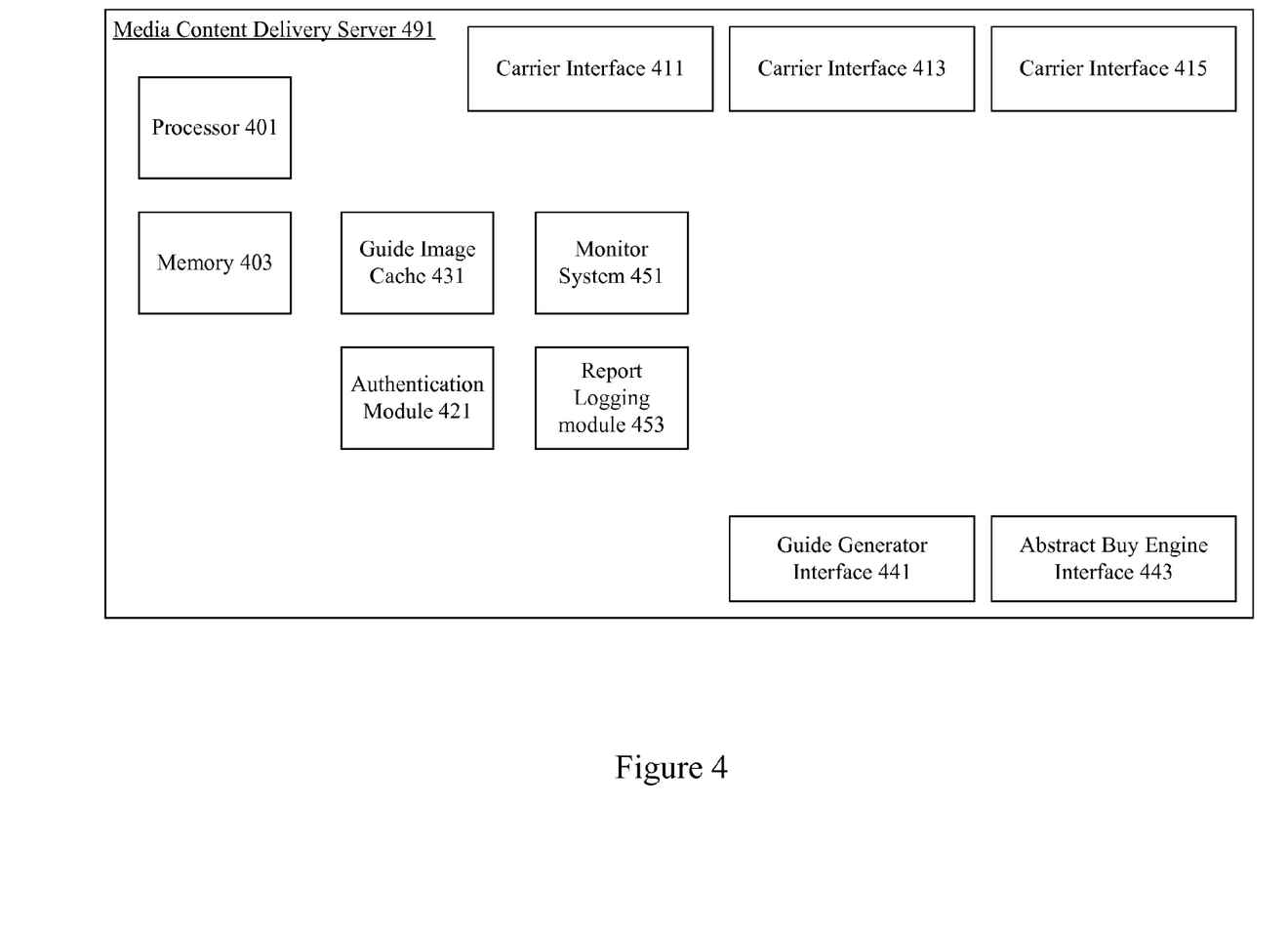
FIG. 4 illustrates a particular example a media delivery server.

FIG. 4 is a diagrammatic representation showing one example of a media content delivery server 491. According to various embodiments, the media content delivery server 491 includes a processor 401, memory 403, and a number of interfaces. In some examples, the interfaces include a guide generator interface 441 allowing the media content delivery server 491 to obtain program guide information. The media content delivery server 491 also can include a program guide cache 431 configured to store program guide information and data associated with various channels. The media content delivery server 491 can also maintain static information such as icons and menu pages. The interfaces also include a carrier interface 411 allowing operation with mobile devices such as cellular phones operating in a particular cellular network. The carrier interface allows a carrier vending system to update subscriptions. Carrier interfaces 413 and 415 allow operation with mobile devices operating in other wireless networks. An abstract buy engine interface 443 provides communication with an abstract buy engine that maintains subscription information.

An authentication module 421 verifies the identity of mobile devices. A logging and report generation module 453 tracks mobile device requests and associated responses. A monitor system 451 allows an administrator to view usage patterns and system availability. According to various embodiments, the media content delivery server 491 handles requests and responses for media content related transactions while a separate streaming server provides the actual media streams. In some instances, a media content delivery server 491 may also have access to a streaming server or operate as a proxy for a streaming server. But in other instances, a media content delivery server 491 does not need to have any interface to a streaming server. In typical instances, however, the media content delivery server 491 also provides some media streams. The media content delivery server 491 can also be configured to provide media clips and files to a user in a manner that supplements a streaming server.

Although a particular media content delivery server 491 is described, it should be recognized that a variety of alternative configurations are possible. For example, some modules such as a report and logging module 453 and a monitor 451 may not be needed on every server. Alternatively, the modules may be implemented on another device connected to the server. In another example, the server 491 may not include an interface to an abstract buy engine and may in fact include the abstract buy engine itself. A variety of configurations are possible.

Figure 5:
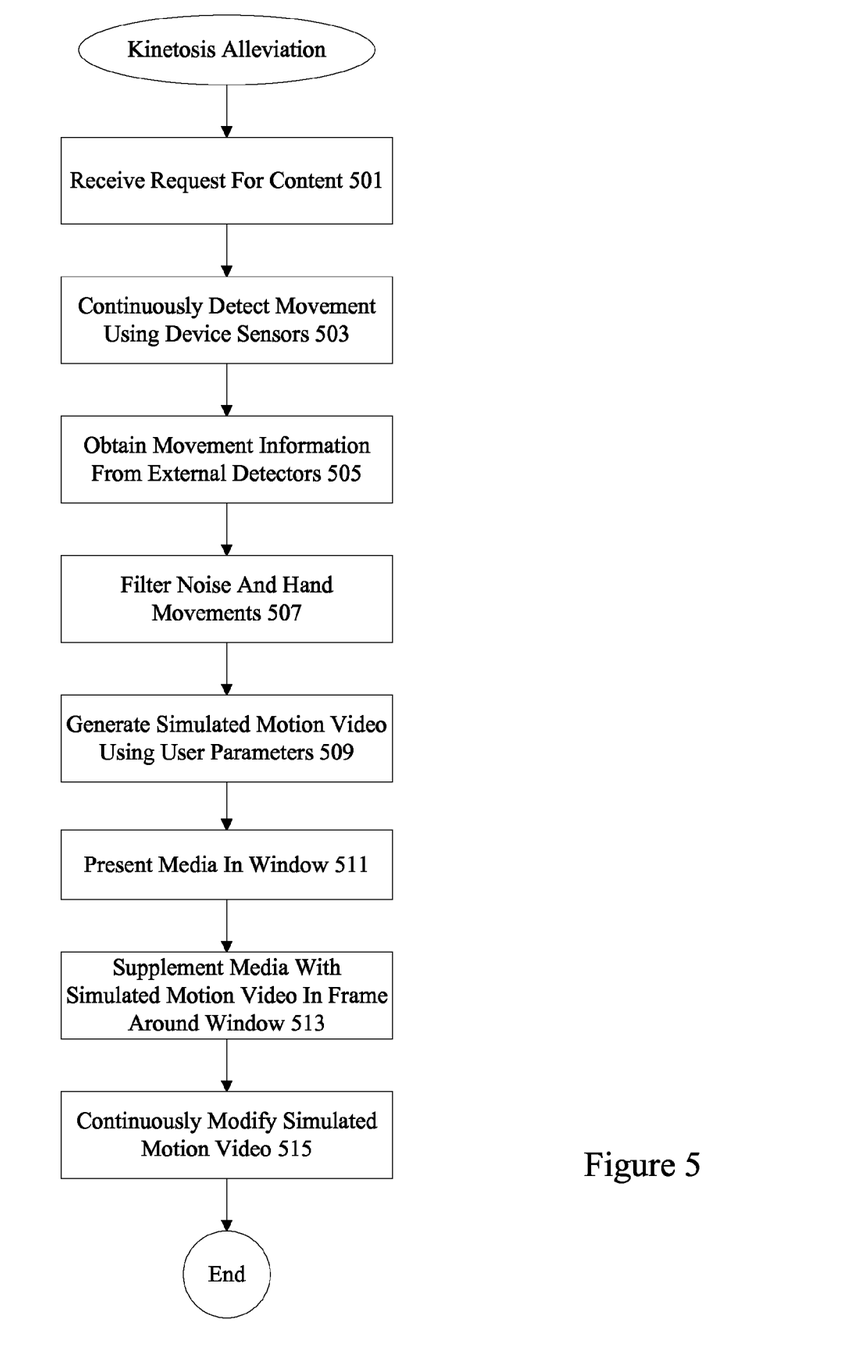
FIG. 5 illustrates a technique for kinetosis alleviation.

FIG. 5 illustrates one example of a technique for kinetosis alleviation. At 501, a request for content is received. According to various embodiments, the content may be video, images, text, data, etc. At 503, device sensors such as accelerometers, global positioning system (GPS) receivers, orientation detectors, gyroscopes, etc., are used to monitor device movement. At 505, external detectors may also be accessed to obtain movement information. External detectors may include vehicle speedometers, altimeters, stability control system sensors, etc. According to various embodiments, noise and hand movements are filtered at 507 to remove motion resulting from jitters and external noise. At 509, simulated motion video is generated using user parameters along with detected movement. User parameters may indicate that magnitude of motion simulation desired. The viewer may also specify the size of a frame area depicting simulated motion, or the opacity of an overlay depicting simulated motion. At 511, media is presented in a window. At 513, media is supplemented with a simulated motion video in a frame around the window. In some embodiments, simulated motion video may be presented in a semi-transparent overlay. At 515, simulated motion video is continuously modified based on continuously detect movements.

Figure 6:
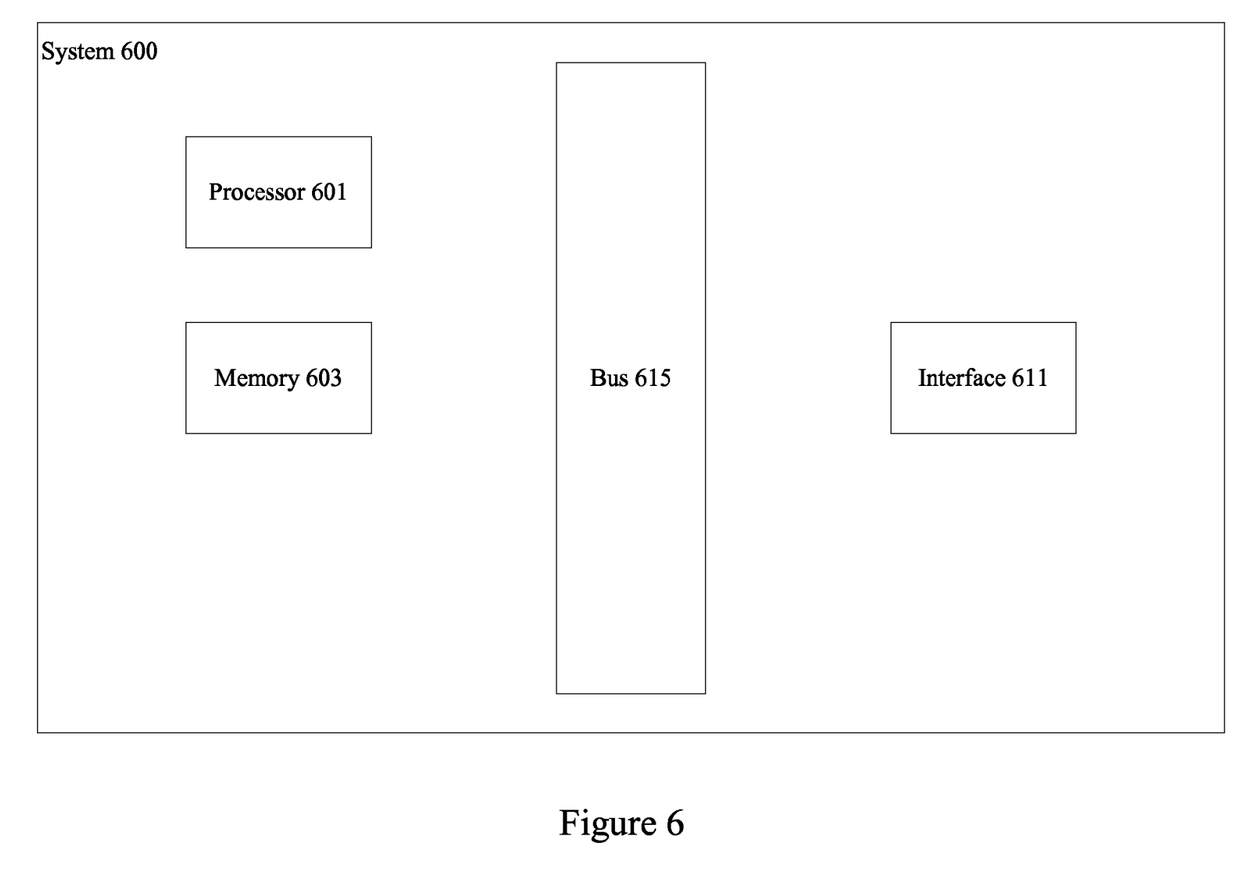
FIG. 6 illustrates a particular example of a computer system.

FIG. 6 illustrates one example of a system. According to particular embodiments, a system 600 suitable for implementing particular embodiments of the present invention includes a processor 601, a memory 603, an interface 611, and a bus 615 (e.g., a PCI bus or other interconnection fabric) and operates as a streaming server. When acting under the control of appropriate software or firmware, the processor 601 is responsible for modifying and transmitting live media data to a client. Various specially configured devices can also be used in place of a processor 601 or in addition to processor 601. The interface 611 is typically configured to end and receive data packets or data segments over a network.

Particular examples of interfaces supports include Ethernet interfaces, frame relay interfaces, cable interfaces, DSL interfaces, token ring interfaces, and the like. In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to various embodiments, the system 600 is a content server that also includes a transceiver, streaming buffers, and a program guide database. The content server may also be associated with subscription management, logging and report generation, and monitoring capabilities. In particular embodiments, functionality for allowing operation with mobile devices such as cellular phones operating in a particular cellular network and providing subscription management. According to various embodiments, an authentication module verifies the identity of devices including mobile devices. A logging and report generation module tracks mobile device requests and associated responses. A monitor system allows an administrator to view usage patterns and system availability. According to various embodiments, the content server 691 handles requests and responses for media content related transactions while a separate streaming server provides the actual media streams.

Because such information and program instructions may be employed to implement the systems/methods described herein, the present invention relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the invention has been particularly shown and described with reference to specific embodiments thereof, it will be understood by those skilled in the art that changes in the form and details of the disclosed embodiments may be made without departing from the spirit or scope of the invention. It is therefore intended that the invention be interpreted to include all variations and equivalents that fall within the true spirit and scope of the present invention.

What is claimed is:

1. A method for preventing or alleviating symptoms of kinetosis, comprising:
   receiving a request for content from a viewer associated with a device, the content including text or video;
   receiving motion information from a motion detector associated with the device, the motion information corresponding to detected movements of the device in relation to a device environment;
   generating motion simulation video using the motion information;
   presenting, in a display of the device, the content to the viewer in a window framed with a motion simulation video, the motion simulation video presenting to the viewer observed movements corresponding to detected movements, wherein the window itself and the content in the window also move, separate from the motion simulation video, such that the positions of the window and the content on the display change relative to a fixed point on the display itself in order to simulate detected movements in addition to the motion simulation video.

2. The method of claim 1, wherein the motion simulation video is presented to alleviate kinetosis.

3. The method of claim 1, wherein the content comprises media content.

4. The method of claim 1, wherein the detector is a global positioning system (GPS) receiver.

5. The method of claim 1, wherein the detector is an accelerometer.

6. The method of claim 1, wherein the detector is a gyroscope.

7. The method of claim 1, wherein the detector is a speedometer or altimeter included in an external device connected to the device.

8. The method of claim 1, wherein the motion simulation video is presented in a semi-transparent overlay.

9. The method of claim 1, wherein motion information is filtered to remove hand movements.

10. The method of claim 9, wherein motion information is filtered to remove noise.

11. The method of claim 1, wherein the device is a mobile device.

12. The method of claim 1, wherein the motion information is received from a plurality of motion detectors included on the device and a vehicle containing the viewer.

13. The method of claim 1, wherein viewer preferences are used to determine the magnitude of compensation in the motion simulation video.

14. The method of claim 1, wherein the motion simulation video is continuously modified based on continuously received motion information.

15. A device, comprising:
   an interface configured to receive a request for content from a viewer, the content including text or video;
   a motion detector configured to detect movement and monitor motion of the device in relation to a device environment and determine motion information;
   a processor configured to present, in a display of the device, the content to the viewer in a window framed with a motion simulation video, the motion simulation video presenting to the viewer observed movements corresponding to detected movements, wherein the window itself and the content in the window also move, separate from the motion simulation video, such that the positions of the window and the content on the display change relative to a fixed point on the display itself in order to simulate detected movements in addition to the motion simulation video.

16. The device of claim 15, wherein the motion simulation video is presented to alleviate kinetosis.

17. The device of claim 15, wherein the motion detector is an accelerometer.

18. The device of claim 15, wherein the motion detector is a gyroscope.

19. The device of claim 15, wherein motion information is filtered to remove hand movements.

20. The device of claim 19, wherein motion information is filtered to remove noise.

21. The device of claim 15, wherein the motion information is received from a plurality of motion detectors included on the device and a vehicle containing the viewer.

22. An apparatus, comprising:
a processor; and
a memory configured to store one or more programs comprising:
instructions for receiving a request for content from a viewer associated with a device, the content including text or video;
instructions for receiving motion information from a motion detector associated with the device, the motion information corresponding to detected movements of the device in relation to a device environment;
instructions for generating motion simulation video using the motion information;
instructions for presenting the content, in a display of the device, to the viewer in a window framed with a motion simulation video, the motion simulation video presenting to the viewer observed movements corresponding to detected movements, wherein the window itself and the content in the window also move, separate from the motion simulation video, such that the positions of the window and the content on the display change relative to a fixed point on the display itself in order to simulate detected movements in addition to the motion simulation video.

* * * * *